Figure 1:
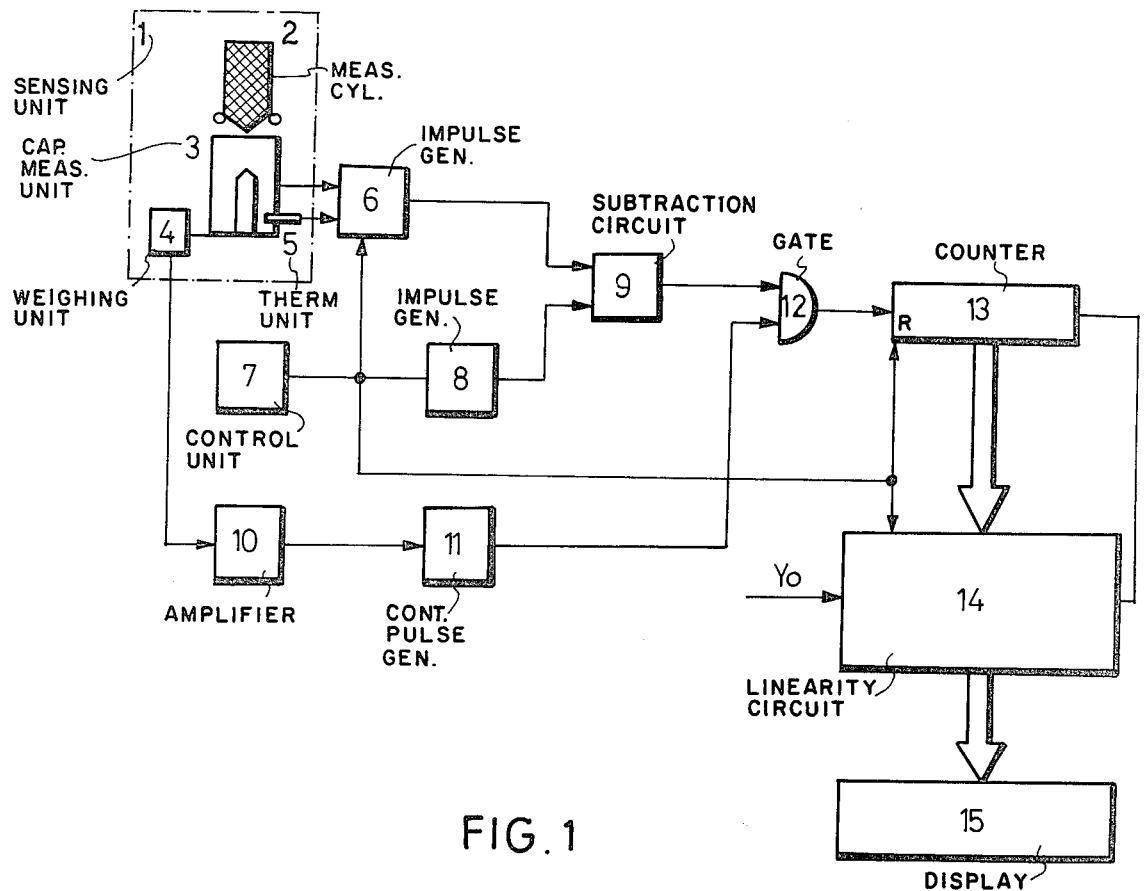

United States Patent [19]

Fabian et al.

[11] 4,287,470
[45] Sep. 1, 1981

[54] DIGITAL HUMIDIMETER

[75] Inventors: Zsolt Fábián; Mihály Samu, both of Gödöllö; Barnabás Balogh, Budapest, all of Hungary

[73] Assignee: Mém Müszaki Intézet, Gödöllö, Hungary

[21] Appl. No.: 11,094

[22] Filed: Feb. 12, 1979

[51] Int. Cl.³ .............................. G01R 27/26
[52] U.S. Cl. .................................... 324/61 R
[58] Field of Search ............ 324/61 R, 61 QS; 73/73, 73/74, 336.5

[56] References Cited

U.S. PATENT DOCUMENTS

| | | | |
|---|---|---|---|
| 3,012,193 | 12/1961 | Breen | 324/61 R |
| 3,227,952 | 1/1966 | Proebster et al. | 324/61 QS |
| 3,761,810 | 9/1973 | Fathauer | 324/61 R |

Primary Examiner—Stanley T. Krawczewicz

[57] ABSTRACT

This invention relates generally to an apparatus for measuring capacitance and resistance and more particularly to a digital humidimeter, which can be used for determining the moisture content of cereals and other powdered, granular or granulated substances.

The apparatus for measuring capacitance and resistance according to the invention is characterized in that two RC impulse generators are provided which generate pulses proportional to the capacitance or resistance to be measured. These generators are triggered by a control circuit. A subtraction circuit is connected on the output of the impulse generators. The subtraction circuit makes possible the measurement of the difference of two capacitances or resistances. The output of the subtraction circuit is connected to one of the inputs of the gate. Another input of the gate is connected to a controllable generator. The output of the gate is connected to a counter. The erase input of the counter is connected to the control circuit. The output of the counter is connected through a linearity circuit to a display. The linearity circuit can modify any monoton function.

3 Claims, 4 Drawing Figures

DIGITAL HUMIDIMETER

This invention relates generally to an apparatus for measuring capacitance and resistance and more particularly to a digital humidimeter, which can be used for determining the moisture content of cereals and other powdered, granular or granulated substances. The apparatus contains a capacitive measuring unit, a circuit for correction according to the volume density and the temperature of the substance to be measured, a circuit for measuring the difference of capacitances, a linearity circuit and a display.

The known devices for measuring the moisture content of different granular or powdered substances, particularly cereals, work generally by determining the dielectric constant of the material to be measured. The determination of the dielectric constant is realized by measuring the capacitance of the measuring cell filled with the substance to be measured, employing a high-frequency measuring method. Such devices are described for example in the Hungarian specification No. 154,475 wherein the apparatus contains a modified Colpitts oscillator. Devices containing Hartley oscillators, are described in the U.S. Pat. No. 3,761,810 and in the Hungarian PS No. 148,670. An apparatus comprising a high-frequency measuring bridge is made known by the U.S. Pat. Nos. 3,691,457 and 3,566,260. Another high-frequency measuring method is described in the U.S. Pat. Nos. 3,559,052 and 3,596,176.

The measuring circuits using alternating voltage with high-frequency—oscillators, bridges—contain numerous discrete elements/resistors, capacitors, transistors-/and therefore the production, setting, calibration and reparation of these circuits demand much work and time. It is not known to realize high-frequency measuring circuits by means of integrated circuits. The favourable digital integrated circuits can not be used for this purpose. It is difficult, to match the high-frequency measuring circuits comprising discrete elements to the digital correction and display circuits.

Other devices for quick determination of the humidity in cereals and other powdered or granular substances are based e.g. on measuring the conductivity /DE PS No. 1,234,052/ the magnetic resonance, the neutron absorption, or on different microwave methods. However, the accuracy of the above methods is unsatisfactory, or the production of devices is not economic, so that these solution are practically insignificant.

The dielectric constant of a material, for example cereals, depends not only on the humidity but also on several other factors among which the measuring frequency, the temperature of the substance to be measured and the volume density are the most important ones. The dielectric constant plotted against the frequency represents a declining function, the temperature function, increases exponentially and the volume density function increases approximately linear.

The devices of high accuracy contain an automatic temperature regulating circuit, as for example the apparatus according to the U.S. Pat. No. 3,761,810, wherein a thermistor and a thermo-element are applied as temperature sensors.

The disadvantages of the thermistors, generally used as temperature sensors, are in the aging, the characteristic-changes and the nonlinearity. The drawback of the thermo-elements consists in the increased costs as a consequence of the increased demands again the measuring amplifier.

At the known devices the reproducibility of the measurements is secured by measuring samples of the same weight. However, the accuracy of the measurements is not satisfactory, especially when measuring cereals, e.g. maize, because the varying dimensions, volume density, position and density of the grains in the measuring cells, which factors influence the accuracy of the measurement in an increased degree. The matter is complicated by that the volume density depends on the moisture content, too.

It is an object of the present invention to provide an improved apparatus which is simple and economic producible.

According to the invention not a high-frequency measuring method is applied, but a method based on time measurements without any polarity change. It is not necessary to measure a sample of a given weight because a compensation according to the volume density is carried out. The new device is more accurate, more simple and more economical than the known devices.

The apparatus for measuring capacitance and resistance according to the invention is characterized in that two RC impulse generators are provided which generate pulses proportional to the capacitance or resistance to be measured. These generators are triggered by a control circuit. A subtraction circuit is connected on the output of the impulse generators. The subtraction circuit makes possible the measurement of the difference of two capacitances or resistances. The output of the subtraction circuit is connected to one of the inputs of a gate. Another input of the gate is connected to a controlable generator. The output of the gate is connected to a counter. The erase input of the counter is connected to the control circuit. The output of the counter is connected through a linearity circuit to a display. The linearity circuit can modify any monoton function.

The device according to the invention can be applied for determining the humidity in cereals and other powdered, granual or granulated substances. The humidimeter according to the invention comprises a capacitive measuring unit which can be filled with the substance to be measured, a correction circuit for the correction according to the volume density of a substance to be measured, a unit for correction according to the temperature of the substance to be measured, an RC impulse generator for converting the capacitance signal of the measuring into pulses a control circuit, a subtraction circuit, a counter with a gate, a control generator, a linearity circuit for modifying any monoton function, and a display.

The device for measuring capacitance and resistance according to the invention will be described in connection with a digital humidimeter with a capacitive unit for measuring the temperature. The device according to the invention can be applied for measuring any capacitance or resistance or the difference of capacitances or resistances.

Figure 2:
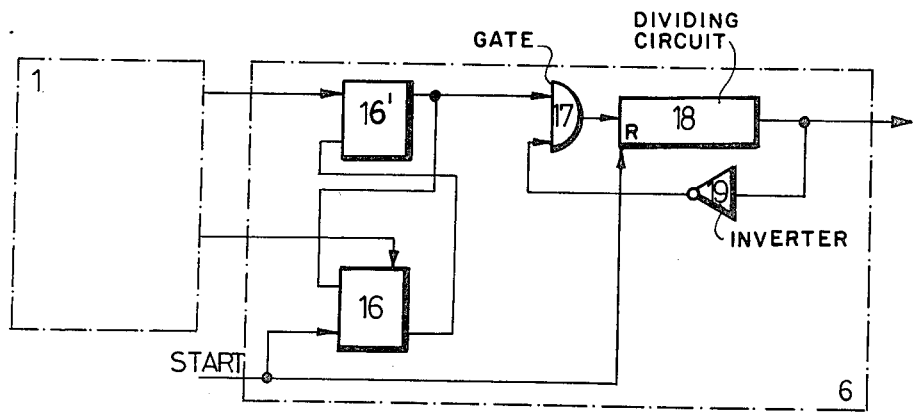
Figure 3:
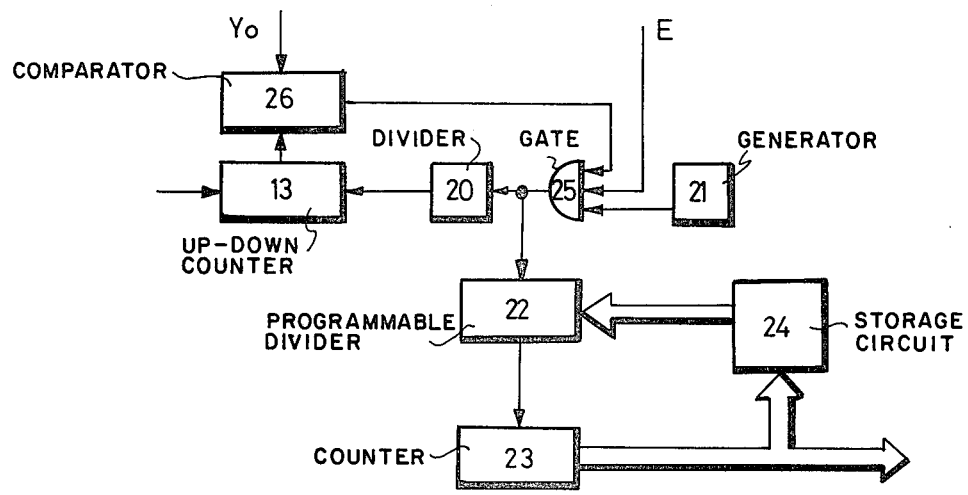

The invention will now be further described by way of example with reference to the accompanying drawings in which FIG. 1 is the block schematic of the digital humidimeter, FIG. 2 is the impulse generator and FIG. 3 is the linearity circuit, according to the invention.

Figure 4:
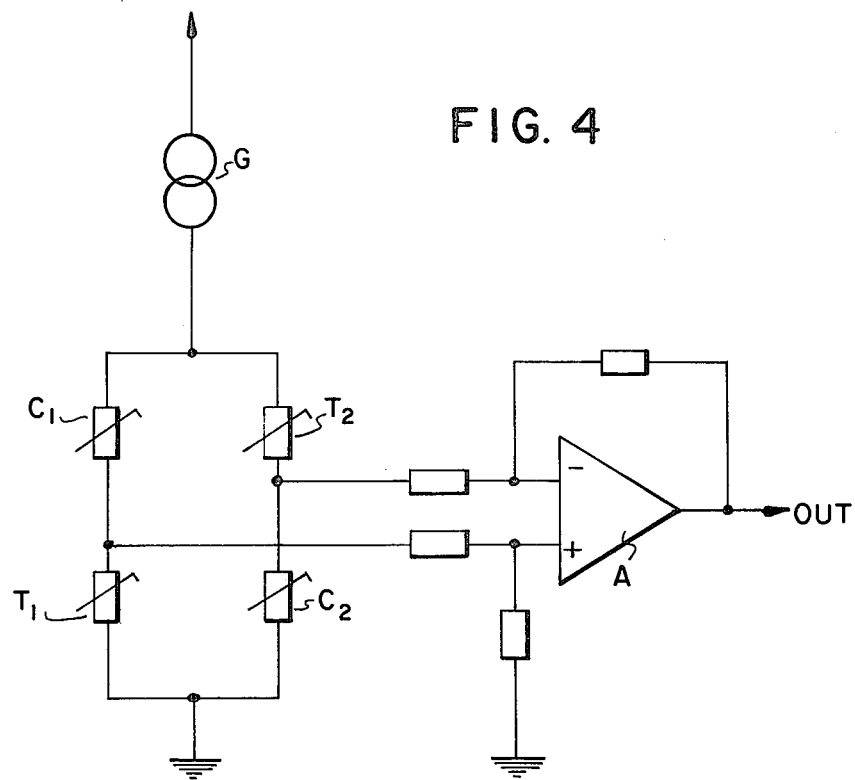

FIG. 4 is the unbalanced bridge with four strain gauges.

The digital humidimeter as shown in FIG. 1 contains a sensing unit 1 consisting of a measuring cylinder 2, cylindrical capacitive measuring unit 3, a weighing unit 4 and a thermometer unit 5. The capacitive unit 3 comprises a cylinder and therein an insulated, preferebly coaxial bar with conic end to secure an even distribution of the substance. The capacitive measuring unit 3 is connected to the input of the RC impulse generator 6. The examplary embodiment of the invention has a capacitive thermometer unit 5 connected to the same point.

The value corresponding to the capacity of the measuring unit filled with a substance with zero moisture content is produced by an RC base impulse generator 8.

The difference between the pulse proportional to the capacity of the measuring unit and corrected according to the temperature of the substance to be measured and the pulse proportional to the zero humidity is produced by the subtraction circuit 9 under control of the control circuit 7.

The output pulses of the controlable generator 11 are counted by the counter 13 during a time permitted by the subtraction circuit 9 through the gate 12. The counter 13 is erased by the control unit 7.

The output signal period of the controlable generator 11 is corrected by the weighing unit 4 according to the dielectric constant-volume density function through the amplifier 10. The corrected dielectric constant-humidity function is made linear by the linearity circuit 14. Therefore the value indicated on the display 15 shows the degree of humidity of the substance in the measuring unit.

This embodiment of the invention works as follows:

The measuring cylinder filled with the substance to be measured secures the prescribed volume of the sample. After opening the bottom of the measuring cylinder 2 the substance falls in the capacitive measuring unit 3 under effect of the gravity. The electrode of the measuring unit 3 secures the even distribution and density of the substance and thereby the reproducibility of the measurement.

Under effect of a START pulse given to the input of the control circuit 7, the control circuit 7 erases the counter 13 and starts, after that the temperature of the thermometer unit 5 has become steady, the RC impulse generators 6 and 8.

Referring now to FIG. 2 a detailed description of the impulse generator 6 will be given. For generating impulses for the measurement of small capacity valves a generator 16, 16' consisting of two monostable multivibrators, and a dividing circuit 18 are provided. The pulse width of the generator 16, 16' is proportional to the capacity of the capacitive measuring unit 3 and the capacitive thermometer unit 5, which is realized preferably by a small ceramic capacitor with an appropriate TK. The START signal of the control circuit 7 erases the dividing circuit 18 and makes the generator 16, 16' produce a pulse train with the above mentioned pulse width. The pulse width on the output of the dividing circuit 18 has been multiplied by the dividing factor by means of the gate 17 and the inverter 19. This pulse width is proportional to the capacity of the capacitive measuring unit 3.

The RC impulse generator 8, which preferably consists of a monostable multivibrator, is times so that the pulse width is the same as the pulse width of the impulse generator 6 when the measuring unit 3 contains a substance of zero humidity. In this way the pulse on the output of the subtraction circuit 9 is proportional to the degree of humidity of the substance in the measuring unit 3, corrected according to the temperature.

The determination of the number proportional to the width of this pulse is carried out in the counter 13 by means of the controlable generator 11 and the gate 12. The period of the pulses of the controlable generator 11 is chosen according to the volume density of the substance to be measured. The volume density of the substance, the given volume of which is secured by the measuring cylinder 2, is determined by the weighing unit 4.

The weighing unit 4 shown in FIG. 1 is realized by an unbalanced bridge comprising four strain gauges. The output voltage of the bridge is proportional to the weight of the measuring unit. This voltage is amplified by the amplifier 10 according to the dielectric constant-volume density function of the substance to be measured. The voltage controlled generator 11 is connected to the output of the amplifier 10. The output signal of the generator 11 is proportional to the volume density of the substance to be measured.

The degree of humidity, corrected according to the temperature and the volume density, is determined by counting the output signals of the controlled generator 11 during a time corresponding to the pulse width of the subtraction circuit 9.

The dielectric constant-humidity function of the materials, and above all that of the cereals, is generally not linear. Therefore the direct indication of the output information of the counter 13 is not advantageous. An embodiment of the linearity circuit 14, shown in FIG. 3, makes linear the dielectric constant-humidity function according to the type of the substance. Essentially the inverse function of the function to be made linear, is replaced by straight lines, the incline of which is stored in the storage circuit 24. The pulse train carrying the measuring information is given on the forward input of the forward-backward counter 13. At the end of the measurement the output of this counter 13 represents a value of the function to be made linear. Thereafter, the corresponding value of the function made linear is determined by means of the output signal of the control circuit 7 given on the input of the gate 25, so that the signals of the generator 21 are given through the gate 25 and the dividing circuit 20 onto the backward input of the counter 13, and through the programable dividing circuit 22 onto the input of the counter 23. In this way, the content of the counter 13 is decreased to an "$y_o$" value /$y_o$ is the value of the function to be made linear when the independent variable is zero given onto the input of the comparator 26. Then the comparator 26 closes the gate 25, and the output of the counter 23 represents the value of the function made linear. The dividing factor of the programable dividing circuit 22 follows the incline changes of the inverse function, according to the output of the counter 23. The output of the counter 23 is connected to the display and/or to another signal-processing unit.

What we claim is:

1. A capacitance and resistance measuring appraratus for the determination of a capacitance value, a resistance value and the difference between two capacitances and two resistances, the apparatus comprising: two RC impulse generators, a control circuit, a subtraction circuit, a gate, a counter, a controllable pulse generator and a display, wherein the resistance or capacitor to be measured is connected to the input of the one pulse generator, the other resistance or capacitor to be measured is connected to the other pulse generator, the output of the control circuit is connected to the triggering inputs of the pulse generators, the outputs of the pulse generators are connected to the input of the subtraction circuit, the output of the subtraction circuit is connected to one input of the gate, the other input of the gate is connected to the output of the controllable pulse generator, a driving signal is connected to the input of the controllable pulse generator, the output of the gate is connected to the input of the counter, the reset input of the counter is connected to the output of the control circuit and the output of the counter is connected to the input of the display.

2. The measuring apparatus of claim 1, for the determination of the moisture content of particulate matter, dust, pieces, or granulates, further comprising a sensing unit, an amplifier and a linearity circuit, wherein the output of the sensing unit which is proportionate to moisture content and the temperature is connected to the one RC pulse generator, the output of the sensing unit which is proportionate to bulk density is connected to the input of the amplifier, the output of the amplifier is connected to the input of the controllable pulse generator, the linearity circuit comprises a comparator, an up-down counter whose output is connected to one input of the comparator, a gate having an input connected to the output of the control circuit, the pulse output of the linearity circuit being connected to the down count input of the counter and its data output being connected to the input of the display.

3. The measuring apparatus of claim 1 for the determination of moisture content, further comprises a volume measuring cylinder, a capacitive measuring unit, a weighing unit and a temperature sensor, wherein the lower part of the volume measuring cylinder is disposed over the capacitive measuring unit, the capacitive measuring unit contains in its interior the temperature sensor, the capacitive measuring unit is affixed to the weighing unit, the output of the capacitive measuring unit and the output of the temperature sensor are connected to the input of the one pulse generator and the output of the weighing unit is connected to the input of the amplifier.

* * * * *